US009308332B2

(12) United States Patent
Heppe (10) Patent No.: US 9,308,332 B2
(45) Date of Patent: Apr. 12, 2016

(54) DEVICE FOR DETECTING MOISTURE, FOR USE WITH AN ARRANGEMENT FOR MONITORING AN ACCESS TO A PATIENT

(75) Inventor: John Heppe, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 103 days.

(21) Appl. No.: 13/806,633

(22) PCT Filed: Jun. 21, 2011

(86) PCT No.: PCT/EP2011/003044
§ 371 (c)(1),
(2), (4) Date: Feb. 4, 2013

(87) PCT Pub. No.: WO2011/160807
PCT Pub. Date: Dec. 29, 2011

(65) Prior Publication Data
US 2013/0150769 A1    Jun. 13, 2013

(30) Foreign Application Priority Data

Jun. 22, 2010  (DE) .......................... 10 2010 024 654

(51) Int. Cl.
| A61M 1/36 | (2006.01) |
| A61M 5/50 | (2006.01) |
| A61M 1/30 | (2006.01) |

(52) U.S. Cl.
CPC .............. *A61M 5/5086* (2013.01); *A61M 1/30* (2013.01); *A61M 1/3653* (2013.01); *A61M 1/3656* (2014.02); *A61M 2205/15* (2013.01)

(58) Field of Classification Search
CPC ............ A61M 1/3653; A61M 1/3656; A61M 2205/13; A61M 2205/15; A61M 2205/3317; A61M 5/168; A61M 5/16831; A61M 5/5086; A61M 1/30; A61M 1/1656; A61M 5/172
USPC .................................................. 604/4.01–6.16
See application file for complete search history.

(56) References Cited

U.S. PATENT DOCUMENTS

| 7,670,289 B1 | 3/2010 | McCall |
| 2002/0198483 A1 | 12/2002 | Wariar et al. |

(Continued)

FOREIGN PATENT DOCUMENTS

| DE | 10 2010 012 545 | 9/2011 |
| EP | 2 550 038 A | 9/2011 |

(Continued)

OTHER PUBLICATIONS

International Preliminary Report on Patentability from PCT/EP2011/003044 mailed on Jan. 10, 2013.

(Continued)

*Primary Examiner* — Philip R Wiest
*Assistant Examiner* — Benjamin Klein
(74) *Attorney, Agent, or Firm* — Kenyon & Kenyon LLP (57) ABSTRACT

The present invention relates to a moisture detection system which takes the form of a covering to be applied to the patient's skin, and to a monitoring system for monitoring a vascular access for a blood-treating apparatus. The covering of the moisture detection system has a flexible substrate material to which an electrically conductive structure having printed conductors is applied as a moisture sensor. In accordance with one aspect of the present invention, because a terminating resistor is not part of a moisture detection system, the device can be inexpensively produced in large quantities. This is of advantage in that the moisture detection system is generally intended for once-only use. With the separate terminating resistor, there is no risk of the terminating resistor being damaged or its resistance changing due to movements on the part of the patient.

22 Claims, 4 Drawing Sheets

(56) References Cited

U.S. PATENT DOCUMENTS

2005/0038325 A1* 2/2005 Moll ............................ 600/300
2010/0010026 A1 1/2010 Rongen

FOREIGN PATENT DOCUMENTS

| WO | 2006/008866 A1 | 1/2006 |
| WO | 2010/091852 A1 | 8/2010 |
| WO | 2011/116943 A1 | 9/2011 |

OTHER PUBLICATIONS

International Search Report from PCT/EP2011/003044 mailed on Oct. 19, 2011.

* cited by examiner

DEVICE FOR DETECTING MOISTURE, FOR USE WITH AN ARRANGEMENT FOR MONITORING AN ACCESS TO A PATIENT

CROSS REFERENCE TO RELATED APPLICATIONS

This is a 371 national phase application of PCT/EP2011/003044 filed Jun. 21, 2011, which claims priority from German Patent Application No. DE 10 2010 024 654.9, filed Jun. 22, 2010.

FIELD OF INVENTION

The present invention relates to a device for detecting moisture, for use with an arrangement for monitoring an access to a patient for an apparatus by which, via a flexible line, a liquid is fed to a patient and/or a liquid is withdrawn from the patient, and in particular for monitoring the vascular access in an extracorporeal blood treatment in which a patient's blood is withdrawn from the patient via a flexible arterial line which has an arterial needle and is fed to the patient via a flexible venous line which has a venous puncturing needle. As well as this, the present invention also relates to an arrangement for monitoring an access to a patient which has a device for detecting moisture. What is more, the present invention also relates to a blood-treating apparatus having an extracorporeal blood circuit which has a flexible arterial line having an arterial needle and which has a flexible venous line having a venous needle, the apparatus for extracorporeal blood treatment having an arrangement for monitoring the arterial and/or venous vascular accesses.

BACKGROUND OF THE INVENTION

In the field of medical technology, there are various known pieces of apparatus by which liquids can be withdrawn from patients or liquids can be fed to the patients via a flexible line. In this case, access is generally gained to the patients by means of a catheter for insertion in organs of the body or a needle for puncturing vessels. During the examination or treatment, it has to be ensured that the access remains in proper order. It is therefore necessary for the patient access to be monitored.

A proper access to the patient is a prerequisite, in particular, for extracorporeal blood treatment devices that comprise an extracorporeal blood circuit. The known pieces of apparatus for extracorporeal blood treatment include for example dialysis apparatus and cell separators, both of which require access to the patient's vascular system. In extracorporeal blood treatment, blood is withdrawn from the patient via a flexible arterial line having an arterial puncturing needle and is fed back to the patient via a flexible venous line having a venous puncturing needle.

Despite the vascular access being monitored regularly by the hospital staff there is, basically, a risk of the puncturing needle slipping out of the patient's blood vessel unnoticed. The risk of the puncturing needle slipping out unnoticed also exists with home dialysis. Various arrangements of different designs for monitoring the vascular access are known. The known monitoring arrangements generally rely on the safety arrangements which are provided as standard in the pieces of blood-treating apparatus and which shut off the extracorporeal blood circuit immediately if there is anything wrong with the vascular access.

There are known arrangements for monitoring a vascular access which have a device for detecting moisture to enable blood escaping at the point of puncture to be detected. The known devices for detecting moisture which are used in the known monitoring arrangements for the patient access take the form of pads to be applied to the point of puncture. The pad is composed of an absorbent material in which a sensor of liquid is embedded.

WO 2006/008866 A1 and U.S. Pat. No. 6,445,304 B1 for example describe devices for detecting moisture which are made of an absorbent material which is applied to the skin. The known pads are characterized by the fact that the sensor of liquid is embedded in the absorbent material.

The sensor of liquid in WO 2006/008866 A1 has two printed conductors which are applied to a substrate material. At one end, the two printed conductors take the form of connecting contacts while at the other end the printed conductors are electrically connected to a terminating resistor. The printed conductors and the terminating resistor are printed on the substrate material. Conductive ink is used for this purpose.

Whereas the printed conductors can be printed on the substrate material with relatively little production-related cost or complication, the production of a printed terminating resistor having a defined resistance which is to be within relatively tight tolerances is found to be relatively problematic. On the one hand it has proved that printed terminating resistors may be subject to relatively wide production-related tolerances. On the other hand it has been seen that the alternating bending strength of terminating resistors printed on a substrate material may be relatively low. This is a problem inasmuch as the terminating resistor is constantly stressed in bending when there are movements on the part of the patient.

The printing of the printed conductors on the substrate material, such for example as a nonwoven material, may be performed in a first printing operation with a silver-containing paste which is dried after the printing operation. In a second printing operation, the terminating resistor can be printed on the substrate material with high-resistance graphite paste. Different forms for the ends of the printed conductors and the terminating resistor are possible in this case.

In a first design, the space on the substrate material which is situated between two ends, which extend parallel to one another, of the printed conductors has a high-resistance graphite paste printed on it. The spacing between the parallel ends of the printed conductors is approximately 1 mm in this case. With this design, it has already been found that even a +/−10% variation in the spacing between the ends of the printed conductors may result in the value of the resistance of the terminating resistor varying by +/−50%. Variations of this kind in the spacing between the ends of the printed conductors may occur due to shrinkage processes in the course of drying or even due to mechanical stresses on the substrate material in practical use such for example as when there are movements on the part of the patient or when a protective film is pulled off the substrate material. A further disadvantage of this design lies in the fact that a small drop of liquid situated on the terminating resistor itself cannot be detected.

In an alternative design, the terminating resistor is not printed on the space situated between two parallel ends of printed conductors and instead the terminating resistor which is printed on the substrate material in a high-resistance paste is in the form of a U whose two sides are connected to the two ends of the printed conductors, i.e. the two ends of the printed conductors continue into the sides of the U-shaped terminating resistor with their width unchanged. The ends of the sides of the U-shaped terminating resistor overlap the two ends of the printed conductors in this case. With this design, it has been found that the variation in the value of the resistance of the terminating resistor can be reduced to +/−30%, and it is not a matter of direct importance for a given spacing to be maintained between the ends of the printed conductors.

Even though lower tolerances can be achieved for the terminating resistor with the alternative design, there are found to be problems in practice in obtaining a repeatable terminating resistor which is printed on the substrate material.

A further disadvantage of printed terminating resistors lies in the fact that sweat from the patient may reduce the value of the resistance of the terminating resistor. Also, there are more stringent requirements set for the biocompatibility of the printed terminating resistor because the terminating resistor may come into contact with the patient's skin.

A further disadvantage of a printed terminating resistor arises from the requirement for a number of moisture sensors which is as large as possible to be arranged on a single printed sheet. The size of the sheets for printing (sheets of nonwoven material) which can be inserted in the printing machine is limited due to the accuracy requirements imposed by the printing when, once the printed conductors printed with the silver-containing paste in the first printing operation have dried, the terminating resistors are to be printed in the graphite paste, in the second printing operation, on the same printed sheet in an exact position next to the printed conductors. Because of the shrinkage of the sheet when the first printing dries, a non-uniform displacement occurs of the second printing relative to the first printing and this increases as the size of the sheets becomes larger and as from a certain sheet size can no longer be accepted because at least some of the terminating resistors are then no longer accurately positioned in the second printing operation. However, for reasons of cost, an attempt has to be made to use sheets which are as large as possible carrying as many individual sensors as possible, because the specific costs of an individual sensor go down as the size of the printed sheet increases. In conflict with this, there is a desire to be able to use moisture sensors, having a terminating resistor, which can be printed particularly inexpensively.

An object underlying the present invention is to provide, for use with an arrangement for monitoring an access to a patient, a device for detecting moisture which can be produced without any great production-related cost or complication, which will reliably withstand the mechanical stresses due, for example, to movements on the part of the patient, which will give repeatable measured results and which has high biocompatibility.

As well as this, an object underlying the present invention is also to provide an arrangement for monitoring an access to a patient, and in particular for monitoring the vascular access in extracorporeal blood treatment, which calls for relatively little production-related cost or complication, which reliably withstands the mechanical stresses due, for example, to movements on the part of the patient, which gives repeatable measured results and which has high biocompatibility. It is also an object of the present invention to provide an apparatus for extracorporeal blood treatment which has an arrangement of this kind for monitoring the vascular access.

The device according to the present invention for detecting moisture takes the form of a covering (pad) to be applied to the patient's skin which has a flexible substrate material to which an electrically conductive structure comprising printed conductors is applied as a moisture sensor. As the electrically conductive structure is applied, or preferably printed, on to a flexible substrate, the electrically conductive structure is not a component of the substrate.

The device for detecting moisture is characterized in that the electrically conductive structure has two printed conductors, with one end of the first printed conductor and one end of the second printed conductor having a first pair of connecting contacts and the other end of the first printed conductor and the other end of the second printed conductor having a second pair of connecting contacts. The first pair of connecting contacts serves to connect to the arrangement for monitoring the vascular access whereas the second pair of connecting contacts serves to connect to the terminating resistor. Because the terminating resistor is not part of the device for detecting moisture, the device can be inexpensively produced in large quantities.

The connecting contacts are preferably formed from the ends of the printed conductors, i.e. it is preferable for the ends or end sections of the printed conductors to be formed as connecting contacts. In this case it is preferable for the connecting contacts to lie on one side of the pad.

Whereas the device for detecting moisture is generally intended to be used only once, the terminating resistor, being a separate component, can be reused repeatedly after a cleaning operation which may possibly be necessary.

Because there is not a terminating resistor present on the flexible substrate material but one is provided separately, there is no risk that the terminating resistor might be damaged due to movements on the part of the patient. What is more, there is also no risk of the resistance of the terminating resistor being able to change as a result of alternating bending stresses due to movements on the part of the patient.

Because the terminating resistor does not come into contact with the patient's skin in practice, there is no necessity for the terminating resistor to be produced from a biocompatible material and there is no risk that sweat from the patient might reduce the value of the resistance of the terminating resistor.

What may be used as a terminating resistor is a conventional resistor which does not have to be applied to the flexible substrate material. Resistors which meet tight tolerances are available at low cost. The terminating resistor may for example be an SMD resistor (miniature resistor). The tolerance on the value of the resistance of such resistors is generally only +/−1%. Even should the SMD resistor come into contact with the patient's skin, the SMD resistor has better biocompatibility than a directly printed resistor.

With the two printed conductors, the terminating resistor makes it easier for the device for detecting moisture to be checked for serviceability by making a measurement of the resistance between the first pair of connecting contacts. If the moisture sensor is serviceable, the resistance measured between the connecting contacts will be the sum of the resistance of the terminating resistor and the resistances of the two printed conductors.

The use of separate terminating resistors has the advantage that a large number of individual sensors can be arranged on one printed sheet, because the shrinkage of the printed sheet is immaterial to the accurate positioning of the terminating resistor when this resistor is external. Also, the printing operation for applying the terminating resistors is dispensed with, thus saving production costs for the printing.

The device for detecting moisture may be designed to take different forms. It may not only be used in blood-treating apparatus which create a vascular access by means of a needle or catheter but is also basically suitable for use in other apparatus. Consequently, the device according to the present invention for detecting moisture is not confined to use in arrangements for monitoring an access to a patient.

A further possible area of application for the device according to the present invention for detecting moisture is for example the monitoring of connectors in medical technology, such for example as Luer connectors or Luer lock connectors.

Connectors of this kind comprise a male and a female part of the connector which can be connected together with an airtight and liquid-tight seal. Leaks may occur if the connectors are not properly connected. Luer connectors and Luer lock connectors are found for example on the system of flexible lines of an extracorporeal blood circuit. In this case the connectors may be monitored by the device according to the present invention to allow a blood loss due to a leak to be detected.

For monitoring leaks from Luer or Luer lock connectors, the device for detecting moisture (the pad) should be of a special design. For this application, the outside dimensions of the pad should be of a size such that the connector or connectors to be monitored can be wrapped as completely as possible in the pad. When the connector is being wrapped, that side of the sensor on which the printed conductors are printed should be directed inwards so that any liquid escaping from the connector can make its way straight onto the printed conductors. Means for fastening the pad to the connector and/or to the flexible line connected to the connector may be provided on the pad and/or the connector and/or on the flexible line. Means for sticking the pad firmly to the connector and/or the flexible line, such for example as adhesive strips, are preferably provided.

The two printed conductors which lead to the connecting contacts may be of different forms. They may each comprise a plurality of portions which are connected together electrically. All that is crucial is that the ends of the printed conductors have connecting contacts to enable on the one hand the monitoring arrangement and on the other hand the terminating resistor to be connected.

Basically, the two printed conductors may follow any desired path on the substrate material. However, to increase sensitivity, they should, as far as possible, be arranged to lie next to one another on the substrate material for their entire length. The entire area available on the substrate material should, as far as possible, be used in this case.

A preferred embodiment makes provision for the first and second pairs of connecting contacts to be arranged on a connecting member belonging to the covering. In this way, all the connecting contacts are easily accessible from one side. The connecting contacts are preferably arranged to be situated next to one another on the connecting member, thus enabling contact to be made with them easily.

In a further preferred embodiment, the two printed conductors each have two portions, with those ends of the two portions which are to be connected together of each printed conductor each being arranged on the connecting member. This embodiment allows the portions of the printed conductors to be electrically connected at the connecting member. The fact of the ends of the printed conductors being run back to the connecting member makes it possible to avoid crossing points at which otherwise the printed conductors would have to cross over one another but without, in so doing, coming into contact with one another. Crossing points of this kind cannot be avoided in printed circuits or can only be avoided at high cost.

An embodiment which is a particular preference provides four pairs of connecting contacts, with two pairs of connecting contacts serving to connect to the arrangement for monitoring the vascular access and to the terminating resistor and two pairs of connecting contacts serving to electrically connect the portions of the printed conductors.

The printed conductors are preferably printed on the substrate material by the screen printing process. The substrate material is preferably a nonwoven material on which the printed conductors can be printed. In the case of a water-based printing ink for example, the surface of the nonwoven material should not be hydrophobic. The nonwoven material also has to be capable of withstanding the stress necessary for the drying of the printing ink, from, for example, heat or UV radiation.

The covering is preferably a U-shaped form but may equally as well be rectangular, circular or oval. The U-shaped covering allows the needle for the patient access to rest on the patient's skin both before and after the covering is applied. However, instead of the covering being U-shaped, it is also possible for an opening for the needle to be passed through to be provided in the covering. However, the needle can then only be inserted once the covering has been applied.

In a further and particularly preferred embodiment, the covering has one or more cut-outs which, together with suitably formed projections on a connecting part of the arrangement for monitoring the patient access which is to be connected to the covering, serve to align the covering and fix it in position.

The arrangement according to the present invention for monitoring an access to a patient, and in particular for monitoring the vascular access in the case of an extracorporeal blood treatment, has the device according to the present invention for detecting moisture. The arrangement for monitoring the patient access preferably has an analyzing unit able to be connected to the device for detecting moisture which, if moisture is detected, triggers an audio and/or visual and/or tactile alarm. A control signal may also be generated to act on the control system of the apparatus by which, via the flexible line, a liquid is being fed to the patient and/or a liquid is being withdrawn from the patient.

The monitoring arrangement preferably has a connecting part, to which the device for detecting moisture is connected to make an electrical connection between the analyzing unit of the monitoring arrangement and the moisture sensor of the device for detecting moisture. The connecting part of the monitoring arrangement is preferably electrically connected to the analyzing unit by a connecting cable of adequate length. Alternatively, it is however also possible for a wireless connection to be made.

In a preferred embodiment the connecting part has a first and a second pair of connecting contacts to which the first and second pair of connecting contacts of the device for detecting moisture can be connected. The first pair of connecting contacts have a connecting cable for making an electrical connection between the analyzing unit of the monitoring arrangement and the moisture sensor of the device for detecting moisture, whereas the second pair of connecting contacts are connected together electrically by the terminating resistor. In this embodiment, the terminating resistor is part of the connecting part of the connecting cable of the monitoring arrangement. It is however possible for the terminating resistor to be provided not in the connecting part of the monitoring arrangement but in the monitoring arrangement, in particular in the analyzing unit. A four-core connecting cable then has to be used, with two cores being intended for the moisture sensor and two cores for the terminating resistor. The terminating resistor can also be provided on the connecting cable or be an integral part of the connecting cable. In this case the terminating resistor can be connected to the connecting cable at any point. A further alternative embodiment provides for a connecting cable having a connecting part with which the connecting cable can be connected to the monitoring arrangement. In this alternative embodiment the terminating resistor may be a component of the connecting part of the connecting cable to be connected to the monitoring arrangement.

The terminating resistor is preferably a miniature resistor (SMD resistor) which can easily be incorporated in the connecting part. SMD resistors have tight tolerances as components and are inexpensive.

The order of the connecting contacts on the connecting part may be as desired. The only thing that is important is that two connecting contacts can be electrically connected to the analyzing unit and two connecting contacts can be electrically connected to the terminating resistor.

The connecting part of the monitoring arrangement may also have two further pairs of connecting contacts to which the associated connecting contacts of the device for detecting moisture which are connected to the ends of the portions of the printed conductors can be connected, to make the electrical connection in the connecting part. The end of the portions of the printed conductors may however also be connected together directly at the connecting member of the detecting device.

The connecting part of the monitoring arrangement preferably takes the form of a clamping device for clamping the covering, and in particular the connecting member of the covering. The clamping device preferably has means by which the device for detecting moisture is so aligned and/or fixed in position that the connecting contacts of the device for detecting moisture are situated opposite the corresponding connecting contacts of the connecting part of the monitoring arrangement. These means may take the form of recesses corresponding to the shape of the device for detecting moisture or projections corresponding to the shape of the cut-outs in the device for detecting moisture. The fixing in position may be achieved by positive interengagement, connection by a force or connection by friction. The connecting contacts themselves may even take the form of means for fixing in position. The connecting contacts may for example be spigots which penetrate into the covering.

The arrangement according to the present invention for monitoring a patient access may form a separate unit or may be part of the apparatus by which a liquid is fed to the patient and/or liquid is withdrawn from the patient and may in particular be part of the apparatus for extracorporeal blood treatment. When the monitoring arrangement according to the present invention is part of the blood-treating apparatus, the monitoring arrangement may make use of certain assemblies or components which are present anyway in the blood-treating apparatus.

BRIEF DESCRIPTION OF THE DRAWINGS

In what follows, an embodiment of the present invention will be explained in detail by reference to the drawings.

In the drawings.

DETAILED DESCRIPTION

Figure 1:
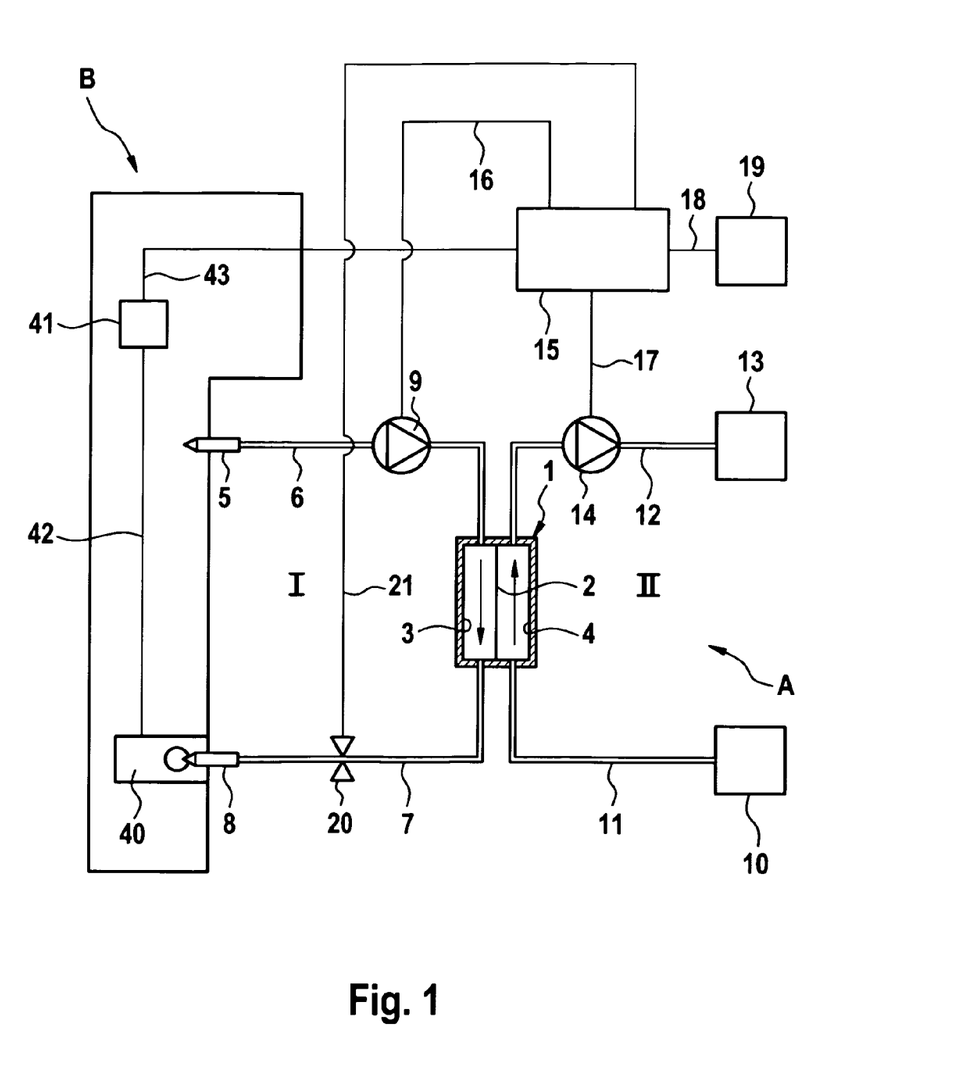
FIG. 1 shows the principal components of a hemodialysis apparatus which has an arrangement for monitoring the arterial and venous vascular accesses.

FIG. 1 shows the principal components of a blood-treating apparatus, and in particular a hemodialysis apparatus, A, which has an arrangement B for monitoring the arterial and venous vascular accesses. In the present embodiment, the monitoring arrangement B is part of the hemodialysis apparatus A. The dialysis apparatus will first be described by reference to FIG. 1.

The hemodialysis apparatus A has a dialyzer 1 which is divided by a semi-permeable membrane 2 into a blood chamber 3 and a dialysis-fluid chamber 4. Connected to the patient's fistula or shunt by means of an arterial puncturing needle 5 is a flexible arterial line 6 which runs to the inlet of the blood chamber 3 of the dialyzer. Leading away from the outlet of the blood chamber 3 of the dialyzer is a flexible venous line 7 which is connected to the patient's fistula or shunt by means of a venous puncturing needle 8. Connected into the flexible arterial line 6 is a blood pump 9 which pumps the blood in the extracorporeal blood circuit I.

The dialysis-fluid circuit II of the dialysis apparatus A comprises a source 10 of dialysis fluid to which a dialysis-fluid infeed line 11 is connected which runs to the inlet of the dialysis-fluid chamber 4 of the dialyzer. Leading away from the outlet of the dialysis-fluid chamber 4 of the dialyzer 1 is a dialysis-fluid takeaway line 12 which runs to a discharge 13. Connected into the dialysis-fluid takeaway line 12 is a dialysis-fluid pump 14.

Responsible for the control of the dialysis apparatus is a central control unit 15 which operates the blood and dialysis-fluid pumps 9, 14 by means of control lines 16, 17. The central control unit 15 is connected by a data line 18 to an alarm unit 19 which gives an audio and/or visual and/or tactile alarm if there is a fault.

Situated on the flexible venous line 7, downstream of the blood chamber 3 of the dialyzer 1, is an electromagnetically actuatable tube clamp 20 which, via a further control line 21, is closed by the central control unit 15 if the venous puncturing needle should slip out of the vascular access and moisture (blood) should be detected at the point of puncture. What is more, the control unit 15 stops the blood pump 9 on the needle slipping out.

In the present embodiment, the monitoring arrangement B serves to monitor the venous vascular access. The monitoring arrangement B has a device 40 for detecting moisture which is arranged at the point of puncture. This detecting device 40 is shown only schematically in FIG. 1. As well as this, the monitoring arrangement also has an analyzing unit 41 which is electrically connected to the detecting device 40 by a connecting line 42.

Via a data line 43, the analyzing unit 41 of the monitoring arrangement B is connected to the central control unit 15 of the dialysis apparatus A. In the event of blood escaping from the venous needle and/or the point of puncture and wetting the moisture sensor, the analyzing unit 41 generates a control signal, which the central control unit 15 receives via the data line 43 and takes action on the blood treatment process. The control unit 15 stops the blood pump 9 and closes the tube clamp 20. As well as this, the control unit also generates an alarm signal, thus causing the alarm unit 19 to give an audio and/or visual and/or tactile alarm. Data may also be transmitted between the monitoring arrangement B and the dialysis apparatus A wirelessly.

Figure 2:
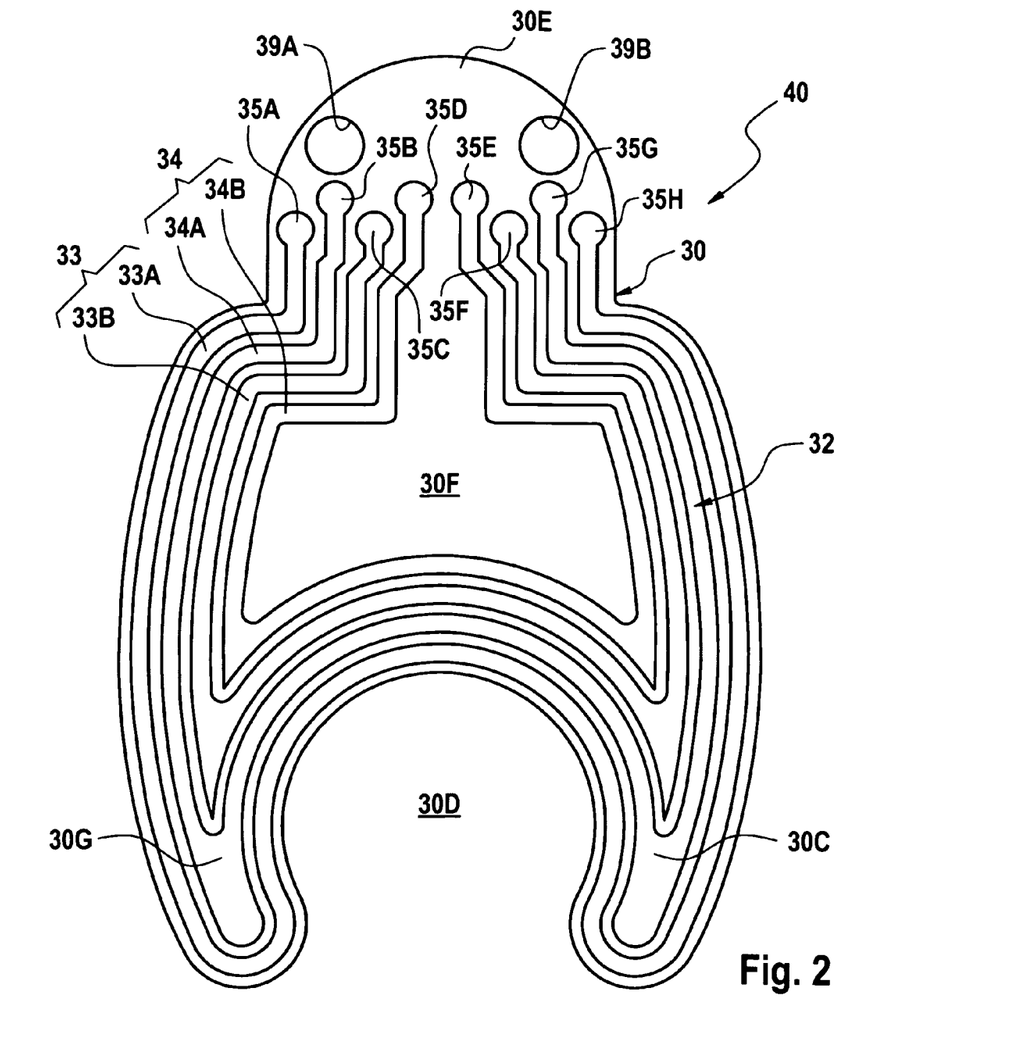
FIG. 2 is a plan view of an embodiment of the device for detecting moisture of the arrangement for monitoring the arterial and venous vascular accesses.
Figure 3:
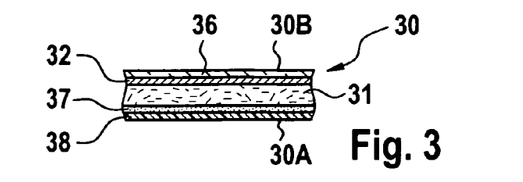
FIG. 3 is a section through the device for detecting moisture.

In what follows, an embodiment of the device 40 for detecting moisture which is to be applied to the patient's skin at the point of puncture will be described by reference to FIGS. 2 and 3. The detecting device 40 is formed from a flexible material as a covering (pad) which is to be applied to the patient's skin. The pad 30 has an underside 30A which is to be applied to the patient's skin and an upper side 30B which is remote from the patient's skin. In the present embodiment the pad 30 is of a U-shaped form. The U-shaped pad 30 has a central section 30F and two side arms 30G, 30C, which extend round the sides of a semi-circular cut-out 30D. Formed on the central section 30F is a connecting member 30E which is situated at the opposite end from the two side arms 30G, 30C and which is semi-circular in shape. The pad 30 comprises a plurality of layers which will be described below (FIG. 3).

The pad 30 has a soft, biocompatible, skin-compatible, substrate material 31 comprising a flexible nonwoven material such for example as a mixture of cellulose/polyester fibres. Due to its open structure, the nonwoven material is permeable both to air and to water vapour. Situated on the upper side of the substrate material 31 is an electrically conductive structure 32 which forms the moisture sensor proper. The electrically conductive structure of the moisture sensor 32 has a first printed conductor 33 and a second printed conductor 34.

The first printed conductor 33 comprises two portions 33A and 33B. The second printed conductor 34 too comprises two portions, 34A and 34B.

The moisture sensor 32 has eight connecting contacts 35A-35H which are arranged on the upper side of the connecting member 30E of the pad 30. The connecting contacts 35A-35H are arranged on the connecting member 30E to lie substantially next to one another. The connecting contacts 35B, 35D, 35E, 35G lie in a first row in this case and the connecting contacts 35A, 35C, 35F, 35H lie in a second row, which means that the connecting contacts are slightly staggered relative to one another.

The first portion 33A of the first printed conductor 33 extends from the first connecting contact 35A along the edge of the pad 30 to the eighth connecting contact 35H, while the first portion 34A of the second printed conductor 34 extends from the second connecting contact 35B alongside the first portion 33A of the first printed conductor to the seventh connecting contact 35G. From the third connecting contact 35C, the second portion 33B of the first printed conductor extends alongside the first section 34A of the second printed conductor to the sixth connecting contact 35F, while the second portion 34B of the second printed conductor 34 extends alongside the second portion 33B of the first printed conductor 33 from the fourth connecting contact 35D to the fifth connecting contact 35E. The individual portions 33A, 33B; 34A, 34B thus each form a non-closed loop of conductor.

The printed conductor 33, 34 and the connecting contacts 35 are printed on the upper side of the substrate material 31. Suitable printing processes for printing the printed conductors and the contact members on the substrate material are familiar to the person skilled in the art. The printed conductors are preferably printed on the substrate material by the screen printing process. Screen printing allows relatively large film thicknesses to be applied, which is necessary for the production on the substrate material of rugged printed conductors. It is preferably a silver-based paste bound in a thermoplastic resin which is applied, the thermoplastic resin evaporating when curing under the prompting of heat takes place.

Present in the present embodiment on the upper side of the substrate material 31 and of the printed conductors 33, 34 is a covering layer 36 which is permeable to moisture. False alarms caused by the printed conductors being touched unintentionally can be avoided in this way. The covering layer 36 also makes the pad easier to clean should it come into contact with liquids. It is however also possible for this covering layer to be dispensed with.

The substrate material 31 is provided on the underside with a layer for adhesion 37 which is impermeable to liquid but permeable to vapour and which is faced with a covering layer 38 and in particular a siliconized paper which can easily be detached from the layer for adhesion. The siliconized paper 38 is pulled off the layer for adhesion 37 before the pad 30 is applied to the patient's skin.

Situated in the connecting member 30E are two circular cut-outs 39A, 39B for aligning the pad 30 and fixing it in position in a connecting part 50 of the monitoring arrangement B, which connecting part 50 will be described in detail in what follows.

Figure 4:
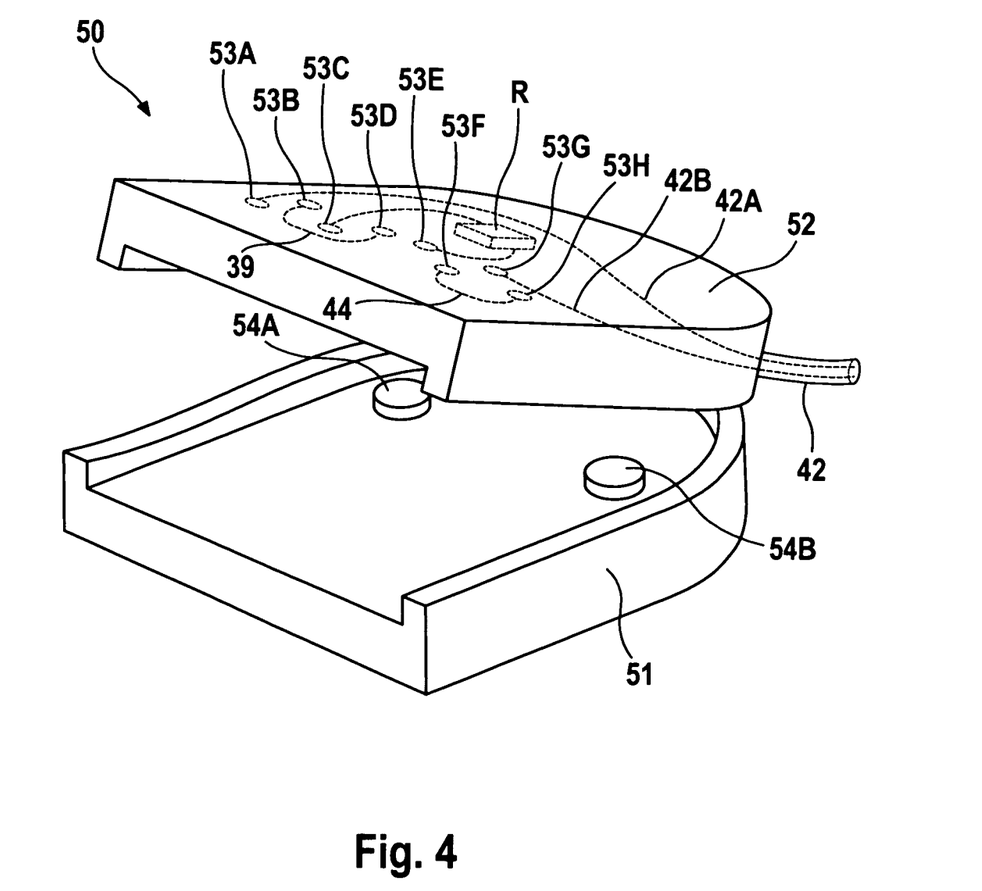
FIG. 4 shows an embodiment of the connecting part of the arrangement for monitoring the vascular access.

FIG. 4 shows an embodiment of the connecting part 50 of the monitoring arrangement B, for connecting the pad 30. The connecting part 50 takes the form of a clamping device for clamping in the connecting member 30E of the pad 30. The connecting part 50 has a bottom clamping part 51 and a top clamping part 52, the connecting member 30E of the pad being able to be inserted in the bottom clamping part 51 as a good fit. Situated in the top clamping part 52 are connecting contacts 53A-53H which are associated with respective ones of the connecting contacts 35A-35H of the pad 30 and which are arranged to be situated next to one another on the inside of the top clamping part 52. Two projections 54A, 54B of circular cross-section on the inside of the bottom clamping part 51, which engage in the circular cut-outs 39A, 39B when the connecting member 30E is inserted, serve to align the pad 30 and fix it in position.

When the connecting member 30E of the pad 30 is clamped between the bottom and top clamping parts 51, 52 of the connecting part 50, an electrical connection is made between the contact members 35A-35H of the pad 30 and the contact members 53A-53H of the connecting part 50.

Connected to the first and seventh connecting contacts 53A, 53G of the connecting part 50 are the two conductors 42A, 42B of the connecting line 42 which runs to the analyzing unit 41 of the monitoring arrangement B. The third and fifth connecting contacts 53C, 53E are connected together electrically by a terminating resistor R. The terminating resistor R may be an SMD resistor (a miniature resistor) built into the top clamping part 52.

The connecting part 50 serves not only to connect the moisture sensor 32 to the analyzing unit 41 of the monitoring arrangement B and to connect the terminating resistor R but also to make the electrical connection between the two portions 33A, 33B; 34A, 34B, of the first and second printed conductors 33, 34 of the moisture sensor 32. For this purpose, the second and fourth connecting contacts 53B, 53D of the connecting part 50 are connected together electrically by a first jumper 39 and the sixth and eighth connecting contacts 53F, 53H are connected together electrically by a second jumper 44. This makes electrical connections between, respectively, the first and second portions 33A, 33B of the first printed conductor 33 and the first and second portions 34A, 34B of the second printed conductor 34 when the connecting member 30E of the pad 30 is clamped in the connecting part 50.

Figure 5:
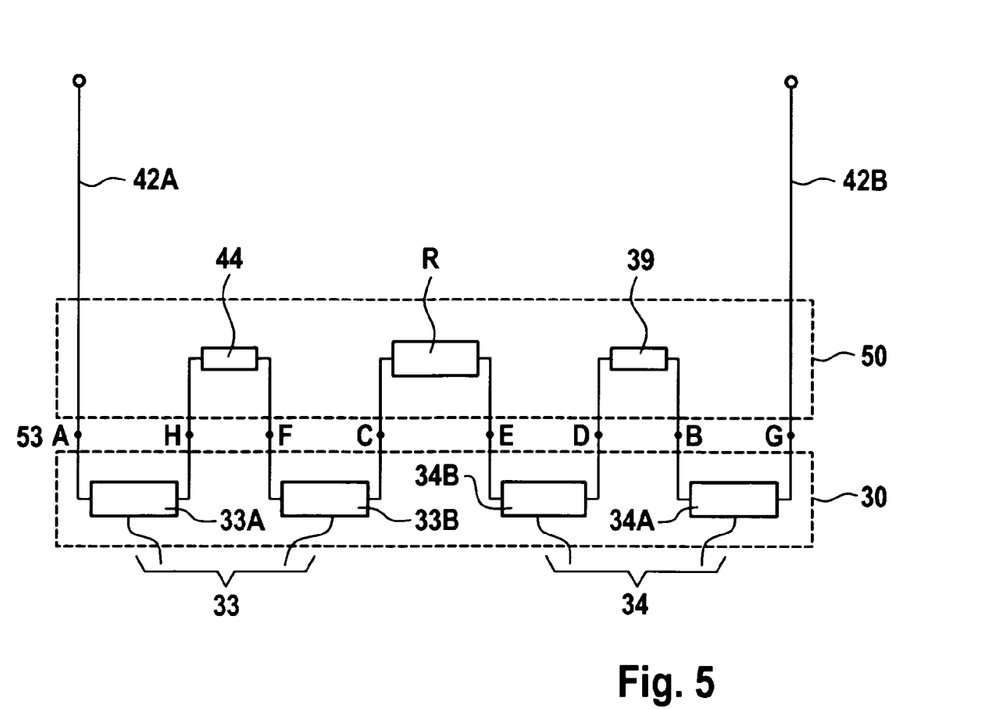
FIG. 5 shows an equivalent circuit diagram of the arrangement for monitoring the vascular access and of the connecting part.

The two portions 33A and 33B are connected in series by the jumper 44 and thus produce the first printed conductor 33. In a similar way, the two portions 34A and 34B are connected in series by the jumper 39 and thus produce the second printed conductor 34. FIG. 5 is an equivalent circuit diagram of the series connections of the portions 33A, 33B and 34A, 34B of the printed conductors 33 and 34 respectively The jumpers 39 and 44 may also be provided on the connecting member 30E of the pad 30 to connect together the connecting contacts 35B, 35D; 35F, 35H of the printed-conductor portions 33A, 33B; 34A, 34B. The jumpers may be printed on the connecting member 30E or may be electrical wires. For the making of contact, the connecting contacts may also be dispensed with, in which case the electrical connection may be made directly at the end of the printed conductors. In this alternative embodiment the corresponding connecting contacts 53B, 53D; 53F, 53H on the connecting part may also be dispensed with.

The overall resistance between the first and seventh connecting contacts 53A, 53G on the connecting part 50, to which connecting contacts 53A, 53G is connected the two-core connecting cable 42 which electrically connects the moisture sensor 32 to an analyzing unit 41 of the monitoring arrangement B, comprises the sum of the resistances of the two printed conductors 33, 34 and of the terminating resistor R. The terminating resistor R is a high-resistance resistor and in particular a resistor whose resistance is more than 100 kohms (high resistance), whereas the printed conductors have a specific resistance of less than 5 ohms/cm (low resistance), such for example as 1-2 ohms/cm.

The analyzing unit 41 of the monitoring arrangement B measures the resistance between the connecting contacts 53A, 53G of the connecting part 50. Should the pad 30 be wetted with liquid, and in particular blood, there is a fall in the resistance measured between the connecting contacts, and the analyzing unit 41 concludes that there is an escape of blood due to a needle disconnection.

The analyzing unit 41 also allows a check to be made on the serviceability of the moisture sensor 32 of the detecting device 40. For this purpose, the analyzing unit 41 measures the resistance between the connecting contacts 53A, 53G. This resistance must correspond to the sum of the resistance of the terminating resistor R and the resistances of the printed conductors when the pad 30 is not wetted with liquid. Should the resistance measured differ from the resistance of the terminating resistor by a preset difference, the analyzing unit 41 finds that the moisture sensor 32 is unserviceable.

The analyzing unit can detect a break in a printed conductor due for example to faulty printing at the time of production or to too high a flow of current if the circuit is overloaded, by virtue of the fact that the analyzing unit finds between the connecting contacts an infinitely high resistance (R→infinite) which is attributable to a circuit which is not closed due to the break in the printed conductor. The analyzing unit is likewise able to detect a misconnected moisture sensor from an infinitely high resistance (R→infinite) between the connecting contacts. Should the printed conductors be touching due to faulty printing at the time of production, this fault can be detected by the analyzing unit by virtue of the fact that an infinitely small resistance (R→zero) which is attributable to a short circuit is measured between the connecting contacts.

The detecting device 40 according to the present invention having the two printed conductors 33, 34 has the advantage that the special path followed by the printed conductors allows the terminating resistor R to be moved off the pad. The pad is easier to manufacture as a result of this. As well as this, the advantage is also obtained of improved strength to resist mechanical stresses and a terminating resistor which is always repeatable regardless of the process used to manufacture the pad.

For use, the siliconized paper 38 is pulled off the pad 30 and the pad is applied to and stuck to the patient's skin with the layer for adhesion or adhesive layer 37. The puncture can then be made with the needle 8. However, because the pad 30 has a cut-out at the end, it is also possible for the pad to be applied and stuck to the patient's skin even after the making of the puncture. It is possible for the connecting part 50 to be connected to the pad 30 before or after the pad is applied to and stuck to the patient's skin.

What is claimed is:

1. A moisture detection system for use with an arrangement for monitoring an access to a patient for an apparatus by which, via a flexible line, a liquid is at least one of fed to the patient via the access or withdrawn from the patient via the access, the moisture detection system comprising:
   a covering configured to be applied to the patient's skin having a flexible substrate material to which an electrically conductive structure comprising printed conductors is applied as a moisture sensor; and
   a terminating resistor;
   wherein the electrically conductive structure has a first printed conductor having a first end and a second end, and a second printed conductor having a first end and a second end,
   wherein the first end of the first printed conductor and the first end of the second printed conductor has a first pair of connecting contacts to connect to the arrangement for monitoring the access, and wherein the second end of the first printed conductor and the second end of the second printed conductor has a second pair of connecting contacts to connect to the terminating resistor which is disposed externally to the covering and which is configured not to contact the patient's skin.

2. The moisture detection system according to claim 1, wherein the first and second pairs of connecting contacts are arranged on a connecting member belonging to the covering.

3. The moisture detection system according to claim 2, wherein the connecting contacts are arranged to lie next to one another on the connecting member.

4. The moisture detection system according to claim 1, wherein the first printed conductor has a first portion and a second portion and the second printed conductor has a first portion and a second portion, wherein two ends of the first portion of the first printed conductor and two ends of the second portion of the first printed conductor are arranged on the connecting member of the covering, and wherein two ends of the first portion of the second printed conductor and two ends of the second portion of the second printed conductor are arranged on the connecting member of the covering.

5. The moisture detection system according to claim 4, wherein one end of the first portion of the first printed conductor and one end of the first portion of the second printed conductor form the connecting contacts making up the first pair of connecting contacts and one end of the second portion of the first printed conductor and one end of the second portion of the second printed conductor form the connecting contacts making up the second pair of connecting contacts.

6. The moisture detection system according to claim 5, wherein the other end of the first portion of the first printed conductor and the other end of the second portion of the first printed conductor form a third pair of connecting contacts and the other end of the first portion of the second printed conductor and the other end of the second portion of the second printed conductor form a fourth pair of connecting contacts.

7. The moisture detection system according to claim 1, wherein the covering has one or more cutouts.

8. The moisture detection system according to claim 1, wherein the covering is U-shaped.

9. The moisture detection system according to claim 1, wherein the substrate material is a nonwoven material.

10. The moisture detection system according to claim 1, wherein the first printed conductor and the second printed conductor are printed on the substrate material by a screen printing process.

11. A monitoring system for monitoring an access to a patient for an apparatus by which, via a flexible line, a liquid is at least one of fed to the patient via the access or withdrawn from the patient via the access comprising a moisture detection system according to claim 1.

12. The monitoring system according to claim 11, wherein the monitoring system is configured to monitor a vascular access in an extracorporeal blood treatment in which a patient's blood is withdrawn from the patient via a flexible arterial line which has an arterial needle and is fed to the patient via a flexible venous line which has a venous puncturing needle.

13. The monitoring system according to claim 11, wherein the monitoring arrangement has an analyzing unit which can be connected to the moisture detection system.

14. The monitoring system according to claim 13, wherein the monitoring arrangement is connected to the analyzing unit via a wireless connection.

15. The monitoring system according to claim 11, wherein the monitoring system has a connecting part to which the moisture detection system can be connected.

16. The monitoring system according to claim 15, wherein the connecting part has a first and a second pair of connecting contacts to which the first and second pairs of connecting contacts of the moisture detection device can be connected, the first pair of connecting contacts being connected to a connecting cable for making an electrical connection between the analyzing unit of the monitoring system and the moisture detection system, and the second pair of connecting contacts being connected together electrically by a terminating resistor.

17. The monitoring system according to claim 16, wherein the terminating resistor is an SMD resistor.

18. The monitoring system according to claim 16, wherein the connecting part of the monitoring system has four further connecting contacts of which two pairs are connected together electrically.

19. The monitoring system according to claim 15, wherein the connecting part of the monitoring arrangement is a clamping device for clamping the cover in position.

20. A blood-treating apparatus having an extracorporeal blood circuit comprises an arterial blood line having an arterial needle and a venous blood line having a venous needle, wherein the blood-treating apparatus comprises a monitoring system according to claim 11.

21. The blood-treating apparatus according to claim 20, further comprising:
a control unit connected to at least one component of the extracorporeal blood circuit, wherein data is transmitted between the control unit and the monitoring system wirelessly.

22. The moisture detection system of claim 1, wherein the arrangement for monitoring an access to a patient is configured to monitor the vascular access in an extracorporeal blood treatment in which a patient's blood is withdrawn from the patient via a flexible arterial line which has an arterial needle and is fed to the patient via a flexible venous line which has a venous puncturing needle.

* * * * *